United States Patent [19]
Steinbrück et al.

[11] Patent Number: 6,087,124
[45] Date of Patent: Jul. 11, 2000

[54] GENETIC TRANSFORMATION OF CILIATE CELLS THROUGH MICROCARRIER BOMBARDMENT WITH DNA-LOADED GOLD PARTICLES

[75] Inventors: Günther Steinbrück, Rottenburg; Thomas Kiy, Frankfurt, both of Germany

[73] Assignee: Hoechst Research & Technologies GmbH & Co. KG, Frankfurt, Germany

[21] Appl. No.: 09/029,444

[22] PCT Filed: Jul. 2, 1997

[86] PCT No.: PCT/EP97/03472

§ 371 Date: Apr. 22, 1998

§ 102(e) Date: Apr. 22, 1998

[87] PCT Pub. No.: WO98/01572

PCT Pub. Date: Jan. 15, 1998

[30] Foreign Application Priority Data

Jul. 3, 1996 [DE] Germany .......................... 196 26 564

[51] Int. Cl.⁷ ...................................... C12P 21/02
[52] U.S. Cl. ...................... 435/69.1; 435/471; 435/258.1
[58] Field of Search ..................................... 435/440, 471, 435/258.1, 69.1

[56] References Cited

U.S. PATENT DOCUMENTS 5,179,022  1/1993  Sanford et al. ..................... 435/440

OTHER PUBLICATIONS

R. Kahn et al., Proc. Natl. Acad. Sci, USA, vol. 90, No. 20, pp. 9295–9299, 1993.
W. Haynes et al., J. of Eukaryotic Microbiology, vol. 42, No. 1, pp. 83–91, 1995.
G. Meyers et al., Gene, vol. 63, No. 1, pp. 31–40, 1988.
M. Yao et al., Proc. Natl. Acad. Sci. USA, vol. 88, No. 21, pp. 9493–9497, 1991.
J. Gaertig et al., Proc. Natl. Acad. Sci, USA, vol. 89, No. 19, pp. 9196–9200, 1992.
D. Cassidy–Hanley et al., vol. 146, No. 1, pp. 135–147, 1997.
B. Hai et al., vol. 94, pp. 1310–1315, 1997.

*Primary Examiner*—James Ketter
*Attorney, Agent, or Firm*—Frommer Lawrence & Haug LLP

[57] ABSTRACT

Genetic transformation of ciliate cells by means of microcarrier bombardment with DNA-loaded gold particles The present invention relates to a process for expressing a heterologous DNA in ciliates. The ciliate cells can be successfully transformed with DNA-loaded gold particles using the method of microcarrier bombardment.

25 Claims, No Drawings

GENETIC TRANSFORMATION OF CILIATE CELLS THROUGH MICROCARRIER BOMBARDMENT WITH DNA-LOADED GOLD PARTICLES

The present invention relates to a process for expressing a heterologous DNA in a novel expression system or host.

Ciliates are single-cell, animal eukaryotes. They possess virtually all the typical properties of eukaryotic cells and at the same time offer the advantage that they can be cultured like prokaryotes. This means that genetically identical clones can be raised from individual cells by means of vegetative replication. In connection with this, very high cell densities can be achieved in continuous or batch culture in the case of some species. Furthermore, like most eukaryotes, ciliates can reproduce sexually. The sexual reproduction, termed conjugation in the case of the ciliates, can be induced by bringing cells of different mating type (mating types are "multiple sexes") into contact under suitable conditions. This property offers the advantage that ciliates can be crossed like higher eukaryotes and strains can, for example, thereby be produced which are homozygous for selected features.

In addition to the features which are typical for most eukaryotes, ciliates possess a number of structural and functional peculiarities which make them particularly suitable both for fundamental cell-biological research and for biotechnological applications. Thus, two types of cell nucleus, which are differentiated in differing ways, are present in almost all ciliate cells: small, transcriptionally inactive, usually diploid micronuclei, and DNA-rich macronuclei which are usually very large. The micronuclei have functions which are in the main generative, i.e. haploid gamete nuclei are formed from them by meiosis during the course of conjugation. The gamete nuclei of two conjugation partners can fuse to form zygote nuclei and produce a new cell generation harboring genetically recombined micronucleus genomes. The zygote nuclei of the new generation produce new macronuclei by means of division. The macronuclei control all the somatic processes of the cells. Their genome is transcribed permanently. Many kinds of drastic elimination and reorganization events take place during the course of macronucleus development. In some species, up to 98% of the micronucleus genome is eliminated, intervening sequences are excised from genes, and coding regions can be rearranged in a completely novel manner ("gene scrambling"). In all ciliates which have been examined in this regard, the genes in the macronucleus are to a greater or lesser extent strongly amplified. Depending on the gene and ciliate species under consideration, the copy numbers can be as high as several millions.

In the very recent past, the molecular biological peculiarities of ciliate genomes have led to some sensational discoveries. Thus, for example, self-splicing introns (ribozymes) were found for the first time in highly amplified ciliate genes (Cech, T. R., B. L. Bass (1986): Ann. Rev. Biochem. 55, 599–629). The structure of telomeres, the terminal structures of linear DNA molecules, and of the telomerases which synthesize them, were likewise elucidated for the first time in ciliates (Blackburn, E. H. (1991): Nature 350, 569–573). It was subsequently found that these fundamental processes and structures, which were initially discovered in ciliates owing to their unusual genome structure, are also characteristic of almost all other eukaryotes; it is just that they are much more difficult to discover and investigate in other eukaryotes.

The peculiarities of the ciliates which have been outlined make the use of these organisms seem particularly rewarding for biotechnological purposes as well. Summarized briefly, the following reasons support this assumption:

1. Ciliates are single-cell eukaryotes which can be raised in clonal cultures, like prokaryotic microorganisms, at high cell density and with relatively short generation times.
2. Their cells exhibit almost all the eukaryotic properties which prokaryotes lack, for example in the areas of DNA replication, of transcription and processing, of translation, of cytoskeletal structure and membrane structure, of endocytic and exocytic processes, etc.
3. Since ciliates are highly developed eukaryotes which have branched off from the common genealogical tree at a late stage, their enzymes, their structural and membrane proteins, and also their metabolic pathways, exhibit a much greater degree of similarity with the corresponding structures and processes in multicell eukaryotes (for example humans) than is the case for comparable structures and processes in prokaryotes (bacteria), insofar as homologous elements occur at all in the latter organisms.
4. All the genes are strongly amplified, to a greater or lesser extent, in the somatic macronucleus genomes of most ciliate species, a feature which results in a high rate of expression even under normal conditions. The degree to which some genes are amplified can be increased by means of suitable measures.

The biotechnological potential which the ciliates can offer for isolating cell-specific or heterologous products has hardly been recognized thus far, and experiments designed to exploit this potential are still in the laboratory test phase. Initial, promising attempts at producing and isolating cell-specific substances on a relatively large scale from ciliates have only recently been published (Kiy, T., A. Tiedtke (1991): Appl. Microbiol. Biotechnol. 35, 14–18; Kiy, T., G. Scheidgen-Kleybold, A. Tiedtke (1996): Enzyme and Microbial Technology 18, 268–274).

Until now, attempts to express heterologous genes or modified, species-specific genes in ciliates have failed principally because the customary methods which are available for transforming eukaryotes resulted in sufficiently high transformation rates in only a few exceptional cases (Gaertig, J., M. Goravsky (1992): Proc. Natl. Acad. Sci. USA 89, 9196–9200). In addition, hardly any suitable selection markers were hitherto available for transformation experiments with ciliates, since it was evidently not possible to use some marker systems in ciliates which are successfully employed generally for eukaryotic transformation (Wünning, I. U., Lipps, H. J. (1983): EMBO J.2, 1753–1757; Meyers, G., E. Helftenbein (1988): Gene 63, 31–40).

One reason for the difficulties experienced in transforming ciliates successfully is probably that the cells are surrounded by a complex and stable cortex structure.

It has recently become known that plant cells, which are surrounded by a strong and rigid cell wall, can be very effectively transformed using the method of microcarrier bombardment (Boynton, J. E., N. W. Giliham, E. H. Harris, J. P. Hosler, A. M. Johnson, A. R. Jones, B. L. Randolp-Anderson, D. Robertson, T. M. Klein, K. B. Shark, J. C. Sanford (1988): Science 240, 1534–1537; Klein, T. M., L. Komstein, J. C. Sanford, M. E. Fromm (1989): Plant Physiol. 91, 440–444; Klein, T. M., E. D. Wolf, R. Wu, J. C. Sanford (1987): Nature 327, 70–73). This biolistic method has by now been optimized (Sanford, J. C., F. D. Smith, J. A. Russell (1993): Meth. Enzymol. 217, 483–509) and has also been employed successfully for transforming mammalian cells (Fitzpatrick-McElligott, S. (1992): Bio/

Technology 10, 1036–1040) and sea urchin eggs (Akasaka, K., A. Nishimura, K. Hijikata, Y. Luchi, J. Morokuma, M. Takahashi, H. Morikawa, H. Shimada (1995): Molecular Marine Biology and Biotechnology 4(3), 255–261). The special features of this transformation method even make it possible to transform intracellular compartments such as chloroplasts or mitochondria (Boynton, J. E., N. W. Gillham, E. H. Harris, J. P. Hosler, A. M. Johnson, A. R. Jones, B. L. Randolph-Anderson, D. Robertson, T. M. Klein, K. B. Shark, J. C. Sanford (1988): Science 240, 1534–1537; Johnston, S. A., P. Q. Anziano, K. Shark, J. C. Sanford, R. A. Butow (1988) Science 240, 1538–1541).

The object of the present invention is to provide a process for expressing a heterologous DNA in a novel expression system or host.

The present relates to a process for expressing a heterologous DNA in an expression system, wherein the expression system comprises transformed ciliate cells. In a preferred embodiment, the heterologous DNA sequence is a gene, and may be of human, animal, plant, bacterial or fungal origin.

The present also relates to a process for preparing the transformed ciliate cells that are useful in expressing a heterologous DNA. The process includes the steps for preparing an expression vector containing the heterologous DNA, and transforming the ciliate cells with the expression vector. The heterologous DNA may be linked, in the sense orientation, to a promoter which is active in ciliates and brings about transcription of the heterologous DNA to be expressed. The heterologous DNA may also be linked to a termination signal which terminates transcription and which is active in ciliate cells. The expression vector may also contain a suitable origin of replication ("ori") which effects replication of the vector in the ciliate cells. When the heterologous DNA is a gene, the expression vector may also contain a signal sequence which leads to the gene product being secreted from the cells.

ciliate cells may be transformed with DNA-loaded gold particles using the method of microcarrier bombardment. In a preferred embodiment of the invention, the plasmid pRT103gus, which contains the heterologous DNA, is for the transformation of the ciliate cells. The plasmid contains the cauliflower mosaic virus 35S promoter, the coding region of the heterologous DNA and a polyadenylation signal.

The ciliate cells useful in the present invention may be selected from the group consisting of Holotrichia, peritrichia, Spirotrichia and Suctoria. The ciliate cells may also be selected from the group consisting of Tetrahymena, Paramecium, Colpidium, Colpoda, Glaucoma, Platyophrya, Vorticella, Potomacus, Pseudocohnilembus, Euplotes, Engelmaniella and Stylonychia. In a preferred embodiment of the invention, the ciliate cells are of the species Stylonychia lemnae.

In the present invention, the heterologous DNA may be modified in vitro. In a preferred embodiment of the invention, the expression product of the heterologous DNA of the transformed ciliate cells is a protein.

The invention also relates to ciliate cells transformed with a heterologous DNA, and a method of preparing same. The transformation may be carried out with DNA-loaded gold particles using the method of microcarrier bombardment.

The experimental mixture which is described below was used for applying the method of microcarrier bombardment with DNA-loaded gold particles for the first time to the transformation of ciliate cells. The experimental results demonstrate that it is possible to transform ciliate cells very simply and effectively by means of this method, using the helium gas-powered apparatus supplied by Biorad. The experiment also demonstrates that the heterologous gene which was used was expressed as a functional gene product in the ciliate cells following transformation. This method therefore offers the possibility of effectively transforming ciliates for biotechnological purposes, both with heterologous ("foreign") genes and with homologous genes which are altered recombinantly where appropriate. It follows from this that the advantageous molecular biological peculiarities of the ciliates, which were mentioned at the outset, can for the first time be exploited on a relatively large scale, for biotechnological applications, using this transformation technique.

EXAMPLES

1. DNA Precipitation onto the Microcarrier Particles

Gold particles (1.6 $\mu$m diameter) are suspended in water at a concentration of 40 mg/ml. 25 $\mu$l of the particle suspension are mixed, while vortexing, with 5 $\mu$l of DNA solution (conc. 1 $\mu$g/$\mu$l in TE buffer), 25 $\mu$l of 2.5 M $CaCl_2$ solution and 20 $\mu$l of 0.1 M spermidine solution. After incubating at room temperature for 10 min, the particles are sedimented by centrifugation in a minifuge (12,000 rpm). 50 $\mu$l of the supernatant are removed and discarded and the residue is resuspended. 3 $\mu$l of the latter are pipetted onto the membrane (rupture disk) for the bombardment.

2. Marker Plasmid Employed

The plasmid pRT103gus was used for the transformation. It carries an ampicillin resistance, the cauliflower mosaic virus 35S promoter, the coding region of the E.coli β-glucuronidase gene and a polyadenylation signal, and is employed successfully for transforming plants.

3. Transformation and Organism Employed

The transformation was carried out using the BIOLISTIC Particle Delivery System (PDS-1,000/He) supplied by BIO-RAD.

Cells of the ciliate species Stylonychia lemnae (ciliates, Hypotrichida), strain Do-6/E, were used for the transformation experiments. The cells had been fasting for one day prior to the experiment. They were concentrated on nylon gauze having a mesh width of 30 $\mu$m and rinsed into a plastic petri dish with the smallest possible quantity of culture medium (Pringsheim's solution) immediately before the experiment. The dish containing the concentrated cells was placed on the floor of the chamber of the transformation appliance. The bombardment was carried out from the greatest possible distance permitted by the appliance. A burst pressure of 450 psi and the corresponding rupture disk were used. Immediately after the bombardment, the cells were diluted in culture medium and feeding with feed organisms (Chlorogonium elongatum) was commenced at a low level.

4. Demonstration of Glucuronidase Activity

As substrate for the glucuronidase, 25 mg of 5-bromo-4-chloro-3-indolylglucuronide are dissolved in 4 ml of DMSO and 40 ml of 10 mM EDTA, 100 mM sodium phosphate buffer, pH 7.0, 0.1% Triton. Two days after the transformation experiment, the transformed ciliate cells were collected on a filter by means of filtration. The filters carrying the ciliate cells were incubated at 32° C. in the substrate solution. The cells are partially lyzed by the Triton-containing solution. After a short time, cells which are expressing the transformed glucuronidase gene can be recognized by a distinct blue coloration. Control cells, which have not been transformed but which have otherwise been treated identically, do not exhibit any blue coloration even after several hours of incubation.

We claim:

1. A process for expressing in ciliate cells a heterologous DNA encoding a protein which comprises:
   providing ciliate cells;
   transforming the ciliate cells with the heterologous DNA, wherein the heterologous DNA is loaded onto gold particles and delivered to the ciliate cells using the method of microcarrier bombardment; and
   providing suitable conditions for the transformed ciliate cells to express the heterologous DNA.

2. The process of claim 1, wherein the ciliate cells are co-transformed with a second heterologous DNA encoding a selectable marker.

3. The process as claimed in claim 1, wherein the DNA sequence is of human origin.

4. The process as claimed in claim 1, wherein the DNA is of animal origin.

5. The process as claimed in claim 1, wherein the DNA is of plant origin.

6. The process as claimed in claim 1, wherein the DNA is of bacterial origin.

7. The process as claimed in claim 1, wherein the DNA is of fungal origin.

8. The process of claim 1, wherein the heterologous DNA loaded onto the gold particles is contained within an expression vector, and is operably linked to a promoter in the sense orientation and to a termination signal.

9. The process of claim 8, wherein the expression vector contains a suitable origin of replication which effects replication of the expression vector in the ciliate cells.

10. The process as claimed in claim 8, wherein the plasmid pRT103gus, which contains the heterologous DNA, is used for the transformation of the ciliate cells.

11. The process as claimed in claim 10, wherein the plasmid contains the cauliflower mosaic virus 35S promoter, the coding region of the heterologous DNA and a polyadenylation signal.

12. The process of claim 8, wherein the expression vector is a plasmid.

13. The process as claimed in claim 1, wherein the ciliates cells are selected from the group Tetrahymena, Paramecium, Colpidium, Colpoda, Glaucoma, Platyophrya, Vorticella, Potomacus, Pseudocohnilembus, Euplotes, Engelmaniella and Stylonychia.

14. The process as claimed in claim 13, wherein cells of the ciliate species Stylonychia lemnae are used as the expression system.

15. The process as claimed in claim 1, wherein the heterologous DNA was modified in vitro.

16. The process as claimed in claim 1, wherein the ciliates cells are selected from the group Holotrichia, Peritrichia, Spirotrichia and Suctoria.

17. A process for delivering a heterologous DNA into ciliate cells which comprises:
    providing ciliate cells; and
    transforming the ciliate cells with the heterologous DNA, wherein the heterologous DNA is loaded onto gold particles and delivered to the ciliate cells using the method of microcarrier bombardment.

18. The ciliate cells transformed according to the process of claim 17.

19. The process of claim 17, wherein the heterologous DNA encodes a protein.

20. The ciliate as claimed in 19, which was transformed with the heterologous DNA-containing plasmid pRT103gus.

21. The ciliate as claimed in claim 20, wherein the plasmid contains the cauliflower mosaic virus 35S promoter, the coding region of the heterologous DNA and a polyadenylation signal.

22. The process of claim 19, wherein the heterologous DNA loaded onto the gold particles is contained within an expression vector, and is operably linked to a promoter in the sense orientation and to a termination signal.

23. The ciliate cells transformed according to the process of claim 22.

24. The process of claim 22, wherein the expression vector further contains a suitable origin of replication which effects replication of the expression vector in the ciliate cells.

25. The process of claim 24, wherein the expression vector is a plasmid.

* * * * *